United States Patent [19]

Kitaguchi

[11] Patent Number: 5,206,027
[45] Date of Patent: Apr. 27, 1993

[54] AMPHIPATHIC COMPOUND AND LIPOSOME COMPRISING THE SAME

[75] Inventor: Hiroshi Kitaguchi, Kanagawa, Japan

[73] Assignee: Fuji Photo Film Co., Ltd., Kanagawa, Japan

[21] Appl. No.: 927,723

[22] Filed: Aug. 11, 1992

Related U.S. Application Data

[63] Continuation of Ser. No. 757,374, Sep. 10, 1991, abandoned.

[30] Foreign Application Priority Data

Sep. 13, 1990 [JP] Japan ................... 2-242981

[51] Int. Cl.$^5$ ............ A61K 9/127; A61K 37/02; C07C 229/00
[52] U.S. Cl. ................... 424/450; 424/417; 530/323; 530/330; 530/331; 554/106; 554/110; 560/169; 560/170; 560/171
[58] Field of Search ............ 424/450, 417; 428/402.2; 260/403, 410; 554/106, 110; 560/171, 169, 170; 530/323, 330, 331; 436/829

[56] References Cited

U.S. PATENT DOCUMENTS 5,116,992  5/1992  Braquet ................ 554/106

FOREIGN PATENT DOCUMENTS 0031090  9/1973  Japan.
0100318  8/1979  Japan.
9109837  7/1991  PCT Int'l Appl..

OTHER PUBLICATIONS

CA 112:115032 (1990).
Leventis et al., Biochemistry 26 3267-3276 (1987).

*Primary Examiner*—Thurman K. Page
*Assistant Examiner*—G. S. Kishore
*Attorney, Agent, or Firm*—Sughrue, Mion, Zinn, Macpeak & Seas

[57] ABSTRACT

An amphipathic compound, which includes a succinic acid moiety and an amino acid moiety and is designed so as to form a stable unilayer liposome, and a negatively charged liposome comprising said amphipathic compound as a membrane-component are disclosed. The amphipathic compound of the present invention gives liposomes which minimize the leakage of a drug encapsulated therein and scarcely undergo association, aggregation or precipitation.

4 Claims, No Drawings

AMPHIPATHIC COMPOUND AND LIPOSOME COMPRISING THE SAME

This is a continuation of application No. 07/757,374 filed Sep. 10, 1991, now abandoned.

FIELD OF THE INVENTION

The present invention relates to an amphipathic compound which includes a succinic acid moiety and an amino acid moiety and is designed so as to form a stable unilayer liposome, and a negatively charged liposome comprising said amphipathic compound as a membrane component.

BACKGROUND OF THE INVENTION

Liposomes are lipid bilayer vesicles. Because it is believed that natural biomembranes have a lipid bilayer structure, liposomes have been used widely as models of biomembranes as in studies on the physicochemical properties thereof. Further, liposomes have been employed as carriers for transporting substances into living organisms, because various substances can be enclosed within the internal aqueous phase or within the membrane of the liposomes and liposomes can fuse with cells or become incorporated into cells.

Thus, liposomes have been used extensively in research, for example, in biology, medicine and pharmacology. Attempts have been made to use liposomes as a carrier for transporting enzymes or carcinostatic substances, for immunological purposes, for achieving mutual interactions with cells or as a drug delivery system.

Although liposomes are widely applicable as described above, liposomes often are disadvantageous because of a rigid membrane structure.

That is to say, it is observed frequently that the orientation of the membrane of a liposome is disordered by a chemical or physical change in the lipids constituting the membrane. As a result, liposomes suffer from leakage of contents or the association or aggregation with other liposomes, resulting in precipitation.

To overcome the disadvantages, attempts have been made to form vesicles using synthetic amphipathic compounds imitating natural phospholipids (refer to, for example, "Liposome", Nojima, Sunamoto and Inoue, (Nankodo), chap. 8). However none of the amphipathic compounds is satisfactory as a drug carrier with a stable vesicle or which is non-toxic.

Known examples of amphipathic compounds having an oligopeptide in the hydrophilic moiety and two long-chain alkyl groups in the hydrophobic moiety include those reported by Ihara et al. (Polym. Commun., 27, 282 (1986); Polymer J., 18, 163 (1986); Chem. Lett., 1713 (1984); and J. Jap. Chem., 543 (1987); and those reported by Shimizu et al. (Chem. Lett., 1341 (1989); Thin Solid Films., 180, 179 (1989); JP-A-2-69498; and JP-A-2-71836) (The term "JP-A" as used herein means an "unexamined published Japanese patent application"). However none of these amphipathic compounds is suitable as a drug carrier because they do not form a unilayer vesicle or the unilayer vesicle, if formed, is converted readily into other structures. Further, every molecule aggregate comprising the compounds is charged positively and thus cannot be used as an appropriate model of a biomembrane containing anionic lipids such as phosphatidylserine or phosphatidylglycerol.

SUMMARY OF THE INVENTION

An object of the present invention is to provide an amphipathic compound, which includes a succinic acid moiety and an amino acid moiety and is designed so as to minimize the leakage of a drug encapsulated within vesicles comprising said compounds and prevent the association, aggregation and precipitation of said vesicles, as well as a negatively charged liposome comprising the same as a membrane component.

The object of the present invention has been achieved by compounds represented by the following formulae (I), (II) or (III) and a liposome comprising the same as a membrane component.

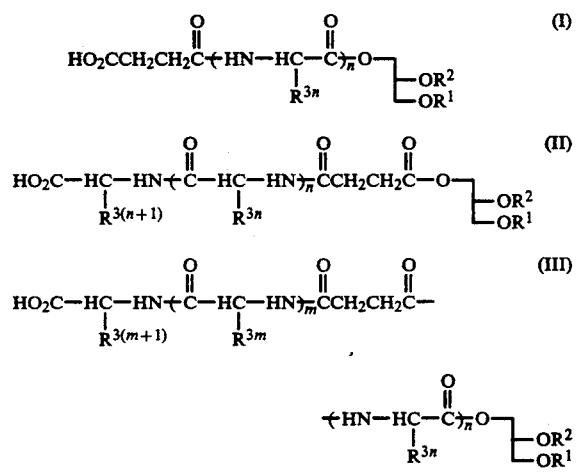

wherein $R^1$ and $R^2$ each represents a straight chain or branched alkyl or acyl group having 8 to 24 carbon atoms, which has or does not have substituents or unsaturated groups;

$R^{3n}$, $R^{3(n+1)}$, $R^{3m}$ and $R^{3(m+1)}$ each represents a side chain residue of an α-amino acid;

n and m each represents an integer of from 0 to 5;

the compound is racemic or optically active and the terminal carboxyl group may form a salt with a cation.

DETAILED DESCRIPTION OF THE INVENTION

In the above formulae, $R^1$ and $R^2$ each represents a straight chain or branched alkyl or acyl group (optionally having unsaturated group(s)) having 8 to 24 (preferably 12, 14, 16 or 20) carbon atoms, which may have further unsaturated group(s) or subtituent(s). Examples of the substituents include an alkylcarbonyl group, an alkoxycarbonyl group and an aryl group, which have preferably from 1 to 10 carbon atoms and more preferably from 3 to 6 carbon atoms, and halogen atoms. Examples of the unsaturated group(s) include double and triple bonds and two or more unsaturated groups may be involved in a single chain. $R^1$ and $R^2$ may be either the same or different from each other. Examples of $R^1$ and $R^2$ include dodecyl, tetradecyl, hexadecyl, myristoyl and palmitoyl groups.

$R^{3n}$, $R^{3(n+1)}$, $R^{3m}$ and $R^{3(m+1)}$ each represents a side chain residue of an α-amino acid, and the side chains of the 20 α-amino acids occurring in nature (refer to, for example, Creighton, "Proteins", (Freeman, 1984)) as well as their analogues are all included therein.

(n+1) in $R^{3(n+1)}$ represents the units of a number. When n is 5, for example, $R^{3(n+1)}$ corresponds to $R^{36}$.

$R^{31}$, $R^{32}$, $R^{33}$, $R^{34}$, $R^{35}$ and $R^{36}$, - - -, $R^{3(n+1)}$ may be either the same or different from each other. The same applies to (m+1) in $R^{3(m+1)}$.

n represents an integer of from 0 to 5 and preferably 0, 1, 2 or 3. The same applies to m.

Regarding the asymmetric carbon atom in the molecule, the compound may be either a racemic body or an optically active body. Further, the carboxyl group located at the terminus of the compound may form a salt together with an appropriate cationic component. Preferable examples of the cationic component include alkali metal ions such as $Na^+$ and $K^+$ and an ammonium ion.

Now particular examples of the compounds of formulae (I) to (III) will be given, though the present invention is not restricted thereby.

| Compound | $R^1$ | $R^2$ | n | $R^{31}$ | $R^{32}$ | $R^{33}$ |
|---|---|---|---|---|---|---|
| | \multicolumn{6}{c}{$R^1-O-CH_2-C(R^2-O)(H)-CH_2-O-C(=O)-(NH)_n-C(R^{3n})(H)-C(=O)-NH-CH_2CH_2CO_2H$} | | | | | |
| 1 | $C_{14}H_{29}$ | $C_{14}H_{29}$ | 1 | H | — | — |
| 2 | $C_{14}H_{29}$ | $C_{14}H_{29}$ | 1 | —CH$_2$OH | — | — |
| 3 | $C_{14}H_{29}$ | $C_{14}H_{29}$ | 2 | H | H | — |
| 4 | —COC$_{15}$H$_{31}$ | —COC$_{15}$H$_{31}$ | 1 | H | — | — |
| 5 | $C_{16}H_{33}$ | $C_{16}H_{33}$ | 2 | H | H | — |
| 6 | —COC$_{13}$H$_{27}$ | —COC$_{13}$H$_{27}$ | 1 | H | — | — |
| 7 | $C_{14}H_{29}$ | $C_{14}H_{29}$ | 3 | H | H | H |
| 8 | —COC$_{15}$H$_{31}$ | —COC$_{15}$H$_{31}$ | 2 | H | H | — |
| 9 | $C_{14}H_{29}$ | $C_{14}H_{29}$ | 1 | —CH$_2$CH$_2$C(=O)NH$_2$ | — | — |
| 10 | $C_{14}H_{29}$ | $C_{14}H_{29}$ | 1 | —CH$_2$CH$_2$CO$_2$H | — | — |
| 11a | $C_{14}H_{29}$ | $C_{14}H_{29}$ | 2 | —CH$_2$OH | —CH$_2$OH | — |
| 11b | $C_{14}H_{29}$ | $C_{14}H_{29}$ | 2 | CH$_3$ | CH$_3$ | — |
| 11c | $C_{14}H_{29}$ | $C_{14}H_{29}$ | 2 | —CH(CH$_3$)$_2$ | —CH(CH$_3$)$_2$ | — |
| 11d | —COC$_{13}$H$_{27}$ | —COC$_{13}$H$_{27}$ | 2 | —CH$_2$CH(CH$_3$)$_2$ | —CH$_2$CH(CH$_3$)$_2$ | — |
| 11e | $C_{14}H_{29}$ | $C_{14}H_{29}$ | 1 | —CH(CH$_3$)$_2$ | — | — |
| | \multicolumn{6}{c}{$R^1-O-CH_2-C(R^2-O)(H)-CH_2-O-C(=O)CH_2CH_2C(=O)-NH-C(R^{3n})(H)-(C(=O))_n-NH-C(R^{3(n+1)})(H)-CO_3H$} | | | | | |
| 12 | $C_{14}H_{29}$ | $C_{14}H_{29}$ | 0 | H | — | — |
| 13 | $C_{14}H_{29}$ | $C_{14}H_{29}$ | 0 | —CH$_2$OH | — | — |
| 14 | —COC$_{13}$H$_{27}$ | —COC$_{13}$H$_{27}$ | 1 | H | H | — |
| 15 | $C_{14}H_{29}$ | $C_{14}H_{29}$ | 1 | H | H | — |
| 16 | —COC$_{15}$H$_{31}$ | —COC$_{15}$H$_{31}$ | 1 | —CH$_2$OH | —CH$_2$OH | — |
| 17 | $C_{16}H_{33}$ | $C_{16}H_{33}$ | 2 | H | H | H |
| 18 | $C_{14}H_{29}$ | $C_{14}H_{29}$ | 0 | —(CH$_2$)$_{\overline{n}}$NH$_2$ | — | — |
| 19 | $C_{12}H_{25}$ | $C_{12}H_{25}$ | 0 | —CH$_2$OH | — | — |
| 20 | $C_{16}H_{33}$ | $C_{16}H_{33}$ | 1 | —CH$_2$OH | H | — |
| 21 | $C_{14}H_{29}$ | $C_{14}H_{29}$ | 2 | CH$_3$ | CH$_3$ | — |
| 22 | $C_{14}H_{29}$ | $C_{14}H_{29}$ | 2 | —CH(CH$_3$)$_2$ | —CH(CH$_3$)$_2$ | — |

-continued

| Compound | R¹ | R² | n | R³¹ | R³² | R³³ |
| --- | --- | --- | --- | --- | --- | --- |
| 23 | $C_{14}H_{29}$ | $C_{14}H_{29}$ | 2 | 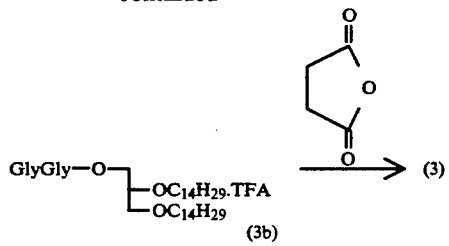 | | — |
| 24 | $\underset{\|}{\overset{O}{\|}}$ $-CC_{13}H_{27}$ | $\underset{\|}{\overset{O}{\|}}$ $-CC_{13}H_{27}$ | 1 | $-CH_2CH(CH_3)_2$ | — | — |

The amphipathic compound of the present invention may be synthesized by starting from 1,2-substituted glcyerol (formula (IV)) and successively introducing the amino acid moiety and succinic acid moiety thereto. The amino acid moiety may be introduced by a conventional method comprising using an amino acid having a protected amino or carboxyl group and condensing with the appropriate condensing agent. Examples of the protecting group and the condensing agent include those described in M. Bodanszky ("Principles of Peptide Synthesis", (Springer-Verlag, New York, 1984) and in "The Practice of Peptide Synthesis", (Springer-Verlag, New York, 1984)). In order to introduce the succinic acid moiety, it is most convenient and useful to employ succinic anhydride.

The compound represented by formula (IV), wherein R¹ and R² each are as defined in formula (I), (II) or (III), may be synthesized by, for example, a method described in J. Am. Chem. Soc., 63, 3244 (1941). It is also commercially available.

Now examples of the syntheses of the compounds of the present invention can provided. Amino acids and protecting groups are expressed in abbreviations in accordance with those commonly used in the art (refer to, for example, the above cited references of Bodanszky). The term "liquid crystal phase transition temperature" as used herein means the temperature at which the crystal phase transits into the liquid crystal phase, determined with a differential scanning calorimeter (DSC) (product of SEIKO Electronics Co., Ltd.).

SYNTHESIS EXAMPLE 1

Synthesis of Compound 3

The compound 3 was synthesized by the following synthesis pathway.

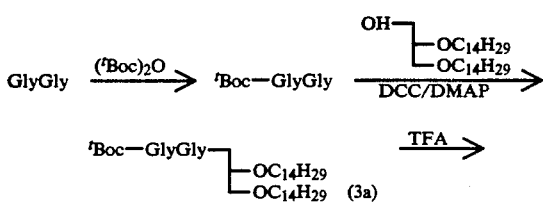

-continued

GlyGly—O $\underset{OC_{14}H_{29}}{\overset{OC_{14}H_{29} \cdot TFA}{\rule{0pt}{0pt}}}$ → (3)

(3b)

Commercially available GlyGly was converted into tBoc-GlyGly in accordance with a conventional method (refer to Izumiya et al ed., "Pepuchido Gosei no Kiso to Jikken" (Maruzen, 1985)).

1.39 g (6 mmol) of tBoc-GlyGly, 2.42 g (5 mmol) of 1,2-o-ditetradecyl-syn-glycerol and 60 mg of N,N-dimethylaminopyridine (DMAP) were dissolved in 20 ml of dimethylformaldehyde (DMF) and 10 ml of methylene chloride. To the resulting solution, 1.3 g of dicyclohexylcarbodiimide (DCC) were added under cooling with water and stirring. The mixture was stirred at room temperature for 24 hours. The dicyclohexyl urea thus precipitated was filtered and the methylene chloride was distilled off from the filtrate under reduced pressure. 50 ml of ethyl acetate was added to the residue followed by successive washing with a 10% aqueous solution of citric acid, water and saline and separating. The dicyclohexyl urea thus precipitated again in the ethyl acetate phase was filtered and the filtrate was concentrated. The obtained residue was purified by silica gel chromatography (n-hexane/ethyl acetate=2/1 by volume) to thereby give 3.37 g (4.8 mmol) of the compound (3a). Yield: 90%.

3.37 g of the protected compound were dissolved in 60 ml of methylene chloride and 30 ml of trifluoroacetic acid (TFA) were added thereto. Then the mixture was stirred at room temperature for 30 minutes. After distilling off the solvent under reduced pressure, the residue was recrystallized from a solvent mixture of ethyl acetate and acetonitrile (1/1) to thereby give 2.87 g (4.03 mmol) of the compound (3b). Yield: 84%. Liquid crystal phase transition temperature: 79° C.

2.85 mg (4 mmol) of the compound (3b) were dissolved in a solvent mixture of 30 ml of methylene chloride and 1.4 ml of triethylamine. Then 0.5 g (5 mmol) of succinic anhydride was added thereto under ice-cooling and stirring. After stirring under ice-cooling for 1 hour and at room temperature for additional 2 hours, the methylene chloride solution was washed successively with 1 N hydrochloric acid, water and saline. After drying over sodium sulfate, the methylene chloride was distilled off under reduced pressure. The residue was recrystallized from ethyl acetate to thereby give 2.49 g (3.56 mmol) of the compound (3).

Yield: 89%. Liquid crystal phase transition temperature 103° C.

SYNTHESIS EXAMPLE 2

Synthesis of Compound (1)

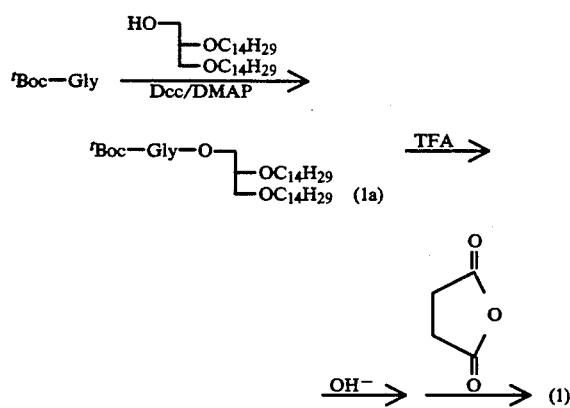

530 mg (3 mmol) of ʹBoc-Gly, 1.21 g (2.5 mmol) of 1,2-o-ditetradecyl-syn-glycerol and 37 mg of N,N-dimethylaminopyridine were dissolved in 15 ml of methylene chloride. To the resulting solution, 600 mg of DCC were added under cooling with water and stirring. The mixture was stirred at room temperature for 24 hours. The dicyclohexyl urea thus precipitated was filtered and the methylene chloride was distilled off from the filtrate under reduced pressure. 50 ml of ethyl acetate was added to the residue followed by successive washing with a 10% aqueous solution of citric acid, water and saline and separating. The dicyclohexyl urea thus precipitated again in the ethyl acetate phase was filtered and the filtrate was concentrated. The obtained residue was purified by silica gel chromatography (n-hexane/ethyl acetate=5/1 by volume) to thereby give 1.55 g (2.4 mmol) of the compound (1a) as a colorless oily product. Yield: 97%.

1.55 g of the protected compound were dissolved in 10 ml of methylene chloride and 5 ml of trifluoroacetic acid was added thereto. Then the mixture was stirred for 30 minutes. After distilling off the solvent under reduced pressure, ethyl acetate and a 4% aqueous solution of sodium carbonate were added thereto followed by extracting and separating. The organic phase was dried over sodium sulfate and the solvent was distilled off under reduced pressure. The residue was dissolved in 15 ml of methylene chloride and cooled with ice followed by adding 250 mg of succinic anhydride thereto. The obtained mixture was stirred under ice-cooling for 30 minutes and at room temperature for 1 hour and then the solvent was distilled off under reduced pressure. The residue was purified by silica gel chromatography (chloroform/methanol=10/1 by volume) and recrystallized from ethyl acetate. Thus 1.1 g (1.68 mmol) of the compound 1 were obtained. Yield: 70%. (2 step) liquid crystal phase transition temperature: 71° C.

SYNTHESIS EXAMPLE 3

Synthesis of Compound 6

The procedure of Synthesis Example 2 was repeated except that the 1,2-o-ditetradecyl-syn-glycerol was replaced with 1,2-o-dimyristoyl-syn-glycerol. Thus the compound 6 was obtained. Liquid crystal phase transition temperature: 70° C.

SYNTHESIS EXAMPLE 4

Synethsis of Compound 4

The procedure of Synthesis Example 2 was repeated except that the 1,2-o-ditetradecyl-syn-glycerol was replaced with 1,2-o-dipalmitoyl-syn-glycerol. Thus the compound 4 was obtained. Liquid crystal phase transition temperature: 78° C.

SYNTHESIS EXAMPLE 5

Synthesis of Compound 12

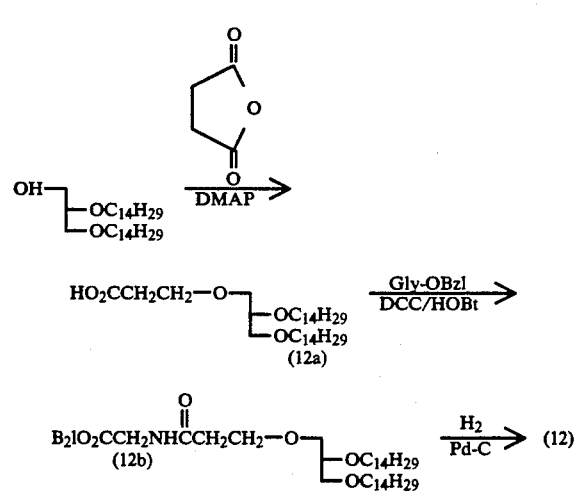

680 mg of succinic anhydride was added to a solution containing 3 g (6.2 mmol) of 1,2-o-ditetradecyl-syn-glycerol and 80 mg of N,N-dimethylaminopyridine in 30 ml of methylene chloride and the resulting mixture was stirred at room temperature for 39 hours. After completion of the stirring, the solvent was distilled off under reduced pressure and the residue was purified by silica gel column chromatography (hexane/ethyl acetate=2/1-1/1 by volume). Thus 2.4 g (4.1 mmol) of the compound (12a) were obtained as a colorless oily product (solidifying at 4° C). Yield: 66%.

1.95 g (2.3 mmol) of the compound (12a), 1.2 g (3.55 mmol) of Gly-OBzl p-toluenesulfoante, 490 µl of triethylamine and 540 mg of 1-hydroxybenzotriazole monohydrate (HOBt) were dissolved in a solvent mixture of 15 ml of methylene chloride and 5 ml of DMF. Then 750 mg of DCC was added thereto under ice-cooling and stirring. The mixture was stirred under ice-cooling for 2 hours and then at room temperature overnight. The dicyclohexyl urea thus precipitated was filtered and the methylene chloride was distilled off from the filtrate under reduced pressure. Ethyl acetate was added to the residue followed by successive washing with a 10% aqueous solution of citric acid, water and saline and separating, The dicyclohexyl urea precipitated again in the ethyl acetate phase was filtered and the filtrate was concentrated. The residue was purified by silica gel column chromatography (hexane/ethyl acetate=3/1-2/1 by volume) to thereby give 2.01 g (2.75 mmol) of the compound (12b). Yield: 83%.

1.97 g (2.69 mmol) of the compound (12b) were dissolved in a solvent mixture of 20 ml of methanol and 20 ml of ethyl acetate. 200 mg of 5% palladium carbon was added thereto followed by conducting atmospheric hydrogenation at room temperature for 3 hours. The catalyst was filtered through Celite. The filtrate was concentrated and crystallized from acetonitrile to thereby give 1.54 g (2.4 mmol) of the compound (12). Yield: 89%. Liquid crystal phase transition temperature: 66° C.

SYNTHESIS EXAMPLE 6

Synthesis of Compound 15

Starting from the compound 12, the procedure of Synthesis Example 5 was repeated to thereby effect the condensation with Gly-OBzl and debenzyl-esterification. After crystallizing from a solvent mixture of ethyl acetate and acetonitrile, the compound 15 was obtained. Liquid crystal phase transition temperature: 86° C.

Liposomes comprising the compounds (I) to (III) of the present invention as a membrane-component may be prepared by a well known method.

Namely, these liposomes may be prepared by vortex swing method (A. D. Bangham, J. Mol. Biol., 13, 238 (1965)), sonication method (C. Huang, Biochem., 8, 344 (1969)), prevesicle method (H. Trauble, Neurosci. Res. Prog. Bull., 9, 273 (1971)), ethanol-injection method (S. Batzri, Biochem. Biophys. Acta., 298, 1015 (1973)), French press extrusion method (Y. Barenhollz, FEBS. Lett., 99, 210 (1979)), cholic acid-removal method (Y. Kagawa, J. Biol. Chem., 246, 5477 (1971)), Triton X-100 batch method (W. J. Gerritsen, Eur. J. Biochem., 85, 255 (1978)), $Ca^{2+}$ fusion method (D. PaPahadjopoulos, Biochem. Biophys. Acta., 394, 483 (1975)), ether-injection method (D. Deamer, Biochem. Biophys. Acta., 443, 629 (1976)), annealing method (R. Lawaczeck, Biochem. Biophys. Acta., 443, 313 (1976)), freezing-/melting method (M. Kasahara, J. Biol. Chem., 252, 7384 (1977)), W/O/W emulsion method (S. Matsumoto, J. Colloid Interface Sci., 62, 149 (1977)), reverse phase evaporation method (F. Szoka, Proc. Natl. Acad. Sci. U.S.A., 75, 4194 (1978)), high-pressure emulsifying method (E. Mayhew, Biochem. Biophys. Acta, 775, 169 (1984)) as well as those described in JP-A-60-7932, JP-A-60-7933, JP-A-60-7934, JP-A-60-12127 and JP-A-62-152531. In the present invention, either one of the methods cited above may be employed and the present invention is not restricted thereby.

As the substance to be encapsulated in the liposome of the present invention, either a hydrophilic drug or a lipophilic drug may be used. Alternately, both of the drugs may be encapsulated simultaneously. Examples of the hydrophilic drug include carcinostatic agents such as adriamycin, actinomycin, mitomycin, 1-$\beta$-arabinofuranosylcytosine, phleomycin and cisplatin, antiviral agents such as interferon, antibiotics such as amino acid glycosides (for example, gentamycin), $\beta$-lactam compounds (for example, sulbenicillin, cefotiam, cefmenoxime), peptide hormone agents such as TRH and insulin, enzyme agents such as lysozyme, asparginase and glycodisae, immunopotentiators such as muramyl dipeptide and muramyl tripeptide and proteins such as immunoglobulin and various toxins.

Examples of the lipophilic drugs include carcinostatic agents such as ansamytocin, immunopotentiators such as TMD-66 (refer to Gann, 74 (2), 192–195 (1983)) and MTP-PE (refer to JP-A-59-163389) and phospholipid derivatives (refer to JP-A-59-163389).

Furthermore, substances (for example, marker, plasmid, DNA, RNA) other than drugs can be used therefor without restriction, so long as they are useful when administered to living organisms.

As a solution to be encapsulated, an aqueous solution prepared by dissolving an appropriate water soluble substance in water may be used. A solution obtained by simply dissolving a drug in water may be used in some cases. As the water soluble substance, various buffers (for example, phosphate buffer and citrate buffer), various salts (for example, sodium chloride, monosodium phosphate, and disodium phosphate), sugars (for example, glucose), amino acids (for example, 1-arginine) or mixtures thereof may be used.

The solution to be encapsulated may further contain, for example, a preservative such as paraben, if required.

The unencapsulated drug and liposomes may be easily separated by, for example, dialysis, filtration (for example, gel filtration) or centrifugation. It is preferable in this procedure to approximate the osmotic pressure of the internal aqueous phase to that of the external aqueous phase as close as possible.

Either one of the compounds of the present invention may be used alone. Alternately, two or more compounds may be mixed together. Further, they may be mixed with other liposome membrane component lipids. Examples of such lipids include various phospholipids, sphingolipids and synthetic lipids.

To further strengthen membrane structure, various procedures, which are known in the field of phospholipid liposomes, may be used in the present invention. Typical examples of such procedures include mixing of sterol or cholesterol and coating with a polysaccharide polymer (refer to JP-A-61-69801).

Different from conventional bilayer membrane component lipids, the compound of the present invention has no hydrophilic moiety of a large radius of hydration. The compound of the present invention nevertheless forms stable liposomes, possibly due to an intermolecular hydrogen bond in the peptide moiety.

EXAMPLES

Examples of the preparation of liposomes comprising the compounds of the present invention as a membrane component will be given.

EXAMPLE 1

30 mg of the compound 3 was dissolved in 10 ml of chloroform. Next, the chloroform was distilled off on a rotary evaporator and the residue was further dried in vacuo. Thus a film of the compound 3 was formed. 3 ml of a Tris buffer solution (6 mM, pH 7.0) containing 150 mM of sodium chloride was added thereto and the mixture was subjected to vortex dispersion. During the procedure, a slight decrease in pH was observed. Thus approximately 20 $\mu$l of 1 N NaOH was added to thereby adjust the pH value to 7. Then the dispersion was ultrasonicated in a bath at 50° C. for 10 minutes and heated to 80° C. for 10 minutes. The dispersion then was filtered under pressure (approximately 11 kg/cm$^2$) 6 times with the use of an extruder (0.2 $\mu$ polycarbonate filter, 55° C.). The determination of the particle size with NICOMP indicated that a monodisperse particle size distribution of an average of 120 nm was obtained. Next, the dispersion was stained with phosphotungstic acid and observed under a transmission electron microscope (TEM). As a result, it was found out that the obtained liposomes were unilayer vesicles.

EXAMPLE 2

A vortex dispersion obtained by the same method as the one described in Example 1 was irradiated with ultrasonic wave of probe type (30 W, 5 minutes). Then it was confirmed, in the same manner as described in Example 1, that unilayer vesicles of an average particle size of approximately 80 nm were prepared.

EXAMPLE 3

The gel/liquid crystal phase transition temperatures of the compounds of the present invention in a phosphate buffer (20 mM, pH 7.0) were measured by using a Privalov type DSC. Table 1 summarizes the results.

TABLE 1

| Compound | Phase transition temp. (°C.) |
| --- | --- |
| 1 | 53 |
| 3 | 49 |
| 4 | 60 |
| 6 | 48 |
| 12 | 48 |
| 15 | 52 |

EXAMPLE 4

A film of 30 mg of the compound 1 was formed in the same manner as described in Example 1. Then 3 ml of a phosphate buffer (20 mM, pH 7.0) containing 50 mM of carboxyfluorescein (CF) was added thereto. Subsequently, the vortex dispersion, ultrasonication in a bath, heating to 80° C. and the treatment with an extruder were performed as in Example 1. No decrease in pH was observed. The obtained dispersion was gel-filtered using Sephadex G-50 equilibrated with a phosphate buffer (20 mM, pH 7.0) containing 150 mM of sodium chloride to thereby separate the unencapsulated CF.

The lipid fraction (average particle size: 120 nm) thus obtained was incubated at 37° C. and the leaking CF was determined by fluorometry. For comparison, liposomes containing CF (average particle size: 140 nm) were prepared by the same method except that the compound 1 was replaced with DPPC (dipalmitoyl phosphatidylcholine). The liposomes were also incubated at 37° C. and the leaking CF was determined. Table 2 shows the results.

TABLE 2

| Time (min.) | Leakage ratio (%) DPPC | Leakage ratio (%) Compound 1 |
| --- | --- | --- |
| 10 | 4.5 | 0.5 |
| 20 | 7.5 | 1.0 |
| 30 | 8.5 | 1.5 |
| 40 | 10 | 2.3 |
| 60 | 11.5 | 3.0 |

As Table 2 shows, the liposomes comprising the compound 1 of the present invention is superior to those comprising DPPC, which is a natural phospholipid, in the barrier effect on CF.

EXAMPLE 5

CF-containing liposomes were prepared by the same method as described in Example 4 except that the compound 1 was replaced with the compounds 3, 4, 6, 12 and 15. Then the leakage at 37° C. was examined. Table 3 shows the leakage ratios of CF after incubating for 1 hour.

TABLE 3

| Lipid | Leakage ratio (%) |
| --- | --- |
| 1 | 3 |
| 4 | 3 |
| 6 | 10 |
| 12 | 11 |
| 15 | 7 |
| DPPC | 11 |

As Table 3 shows, most of the compounds of the present invention are comparable or superior to DPPC, which is a natural phospholipid, in the barrier ability.

Further, it was attempted to prepare liposomes by the same method using the compound 12 a which is an intermediate formed during the synthesis of the compound (12). No CF-containing liposome could be formed. (No fraction corresponding to liposomes was obtained at the gel filtration stage.) That observation suggests that the peptide bond involved in the compound of the present invention might contribute to the stabilization of liposomes.

EXAMPLE 6

The CF-containing liposomes prepared in Example 4 using the compound 1 were incubated at 4° C. The CF-containing liposomes prepared from DPPC showed precipitation after storing at 4° C. for 20 days. On the other hand, the liposomes prepared by using the compound 1 remained in a stable dispersion state after storing more than 4 months. The leakage ratio of the liposomes after 60 days was as low as 1.1%.

EXAMPLE 7

CF-containing liposomes were prepared by the same method as described in Example 4 except that compound 1 was replaced with the compound 4. Further, CF-containing liposomes were similarly prepared by adding 20% and 50%, on a molar basis, of cholesterol to the compound 4. The liposome dispersions were incubated at 37° C. and the leaking CF was determined by fluorometry. Table 4 shows the leakage ratios after incubating for 1 hour.

TABLE 4

| Added cholesterol (%) | Leakage ratio (%) |
| --- | --- |
| 0 | 31 |
| 20 | 3 |
| 50 | <1 |

As Table 4 shows, the barrier effect of the liposomes formed by the compound of the present invention can be highly improved by adding cholesterol. The liposomes, to which 50% of cholesterol was added, were incubated at 4° C. As a result, these liposomes remained in a stage of a stable dispersion for more than 2 months and the CF leakage ratio (%) after incubating for 60 days was less than 1%.

While the invention has been described in detailed with reference to specific embodiments, it will be apparent to one skilled in the art that various changes and modifications can be made to the invention without departing from its spirit and scope.

What is claimed is:

1. A compound represented by formula (I), (II) or (III):

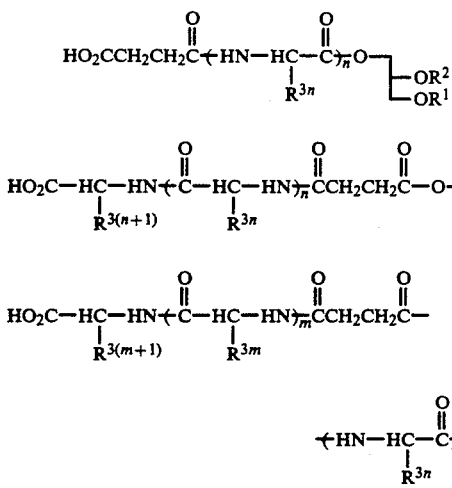

wherein
- $R^1$ and $R^2$ each represents a straight chain or branched alkyl or acyl group having 8 to 24 carbon atoms, which has or does not have substituents or unsaturated groups;
- $R^{3n}$, $R^{3(n+1)}$, $R^{3m}$ and $R^{3(m+1)}$ each represents a side chain residue of an α-amino acid;
- m represents an integer of from 0 to 5;
- n is an integer of from 1 to 5;
- the compound is racemic or optically active and the terminal carboxyl group may form a salt with a cation.

2. The compound of claim 1, wherein $R^1$ and $R^2$ each are a dodecyl group, a tetradecyl group, a hexadecyl group, a myristoyl group or a palmitoyl group.

3. The compound of claim 1, wherein m is 0, 1, 2, or 3 and n is 1, 2 or 3.

4. A liposome consisting essentially of a compound selected from the group consisting of the compounds of formula (I), (II) and (III) of claim 1.

* * * * *